(12) United States Patent
Karg et al.

(10) Patent No.: US 10,932,912 B2
(45) Date of Patent: Mar. 2, 2021

(54) PLUG IN STRUTS FOR GRAFT CAGE

(71) Applicant: DePuy Synthes Products, Inc., Raynham, MA (US)

(72) Inventors: Nicholas Karg, Zuchwil (CH); Steffan Daniel, Zuchwil (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 229 days.

(21) Appl. No.: 16/124,313

(22) Filed: Sep. 7, 2018

(65) Prior Publication Data

US 2019/0076252 A1 Mar. 14, 2019

Related U.S. Application Data

(60) Provisional application No. 62/556,786, filed on Sep. 11, 2017.

(51) Int. Cl.
*A61F 2/28* (2006.01)
*A61F 2/30* (2006.01)

(52) U.S. Cl.
CPC .......... *A61F 2/2803* (2013.01); *A61F 2/2846* (2013.01); *A61F 2/30771* (2013.01); *A61F 2002/285* (2013.01); *A61F 2002/305* (2013.01); *A61F 2002/3092* (2013.01); *A61F 2002/3093* (2013.01); *A61F 2002/3096* (2013.01); *A61F 2002/30471* (2013.01); *A61F 2002/30578* (2013.01); *A61F 2002/30594* (2013.01)

(58) Field of Classification Search
CPC ........ A61F 2/28; A61F 2/2803; A61F 2/2846; A61F 2/30771
See application file for complete search history.

(56) References Cited

U.S. PATENT DOCUMENTS

| | | | |
|---|---|---|---|
| 2017/0216033 A1 | 8/2017 | Daniel et al. | |
| 2017/0216034 A1 | 8/2017 | Daniel et al. | |
| 2017/0354503 A1* | 12/2017 | Larsen | A61F 2/30907 |
| 2018/0193530 A1 | 7/2018 | Barbas et al. | |
| 2019/0015209 A1* | 1/2019 | Scifert | A61F 2/4601 |

* cited by examiner

*Primary Examiner* — Jason-Dennis N Stewart
(74) *Attorney, Agent, or Firm* — Fay Kaplun & Marcin, LLP

(57) ABSTRACT

A system for treating a bone including a graft containment device extending longitudinally from a first end to a second end and including a channel extending therethrough for receiving a graft material therein, the graft containment device including a plurality of fixation openings extending therethrough and a strut extending longitudinally from a first end to a second end and including an attaching portion configured to be attached to the graft containment device and an overhang portion configured to extend beyond one of the first and second ends, when the attaching portion is attached to the graft containment device, the attaching portion including a plurality of coupling elements for engaging the fixation openings of the graft containment device, the overhang portion including an overhang opening configured to receive a bone fixation element for fixing the strut to a bone.

20 Claims, 2 Drawing Sheets

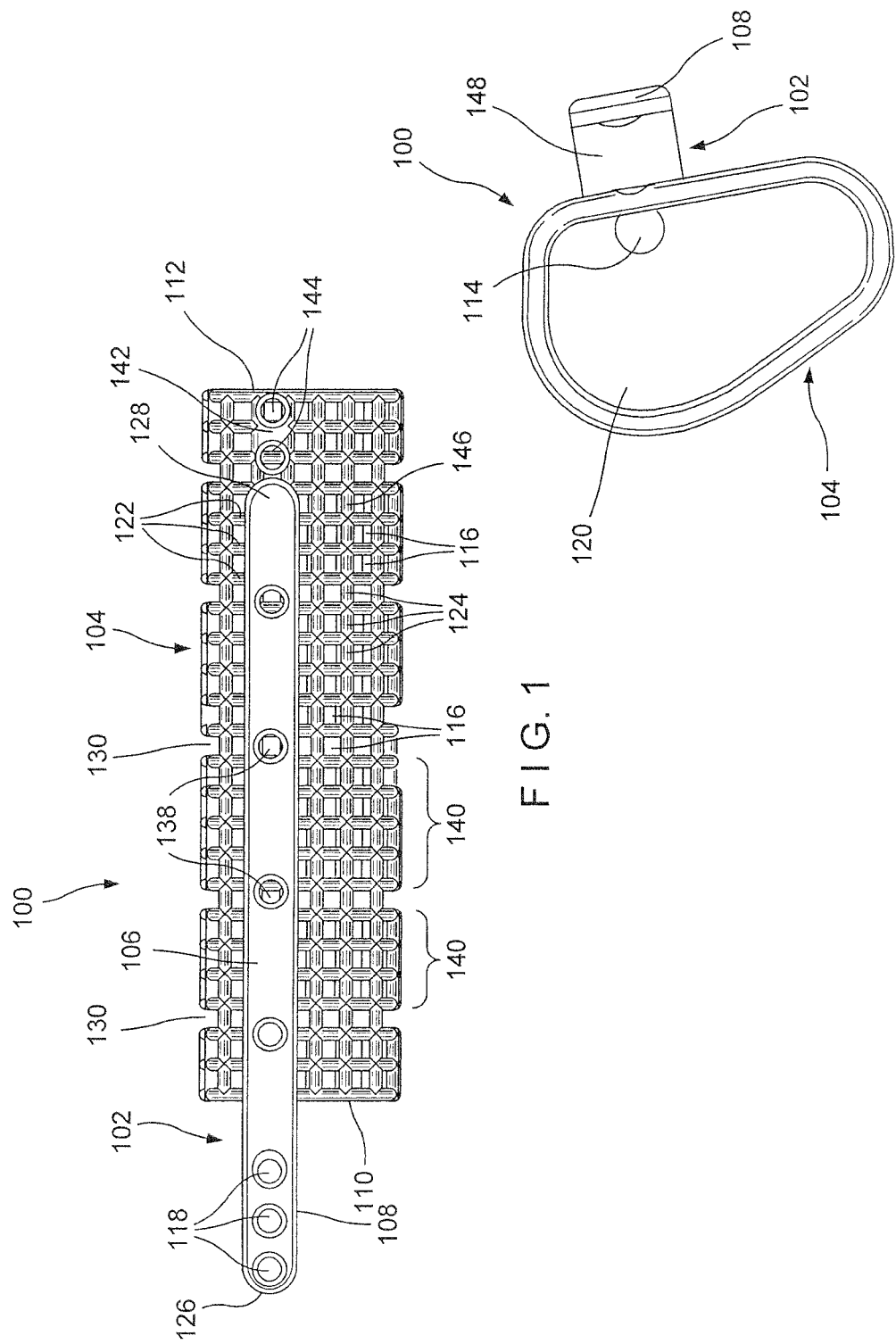

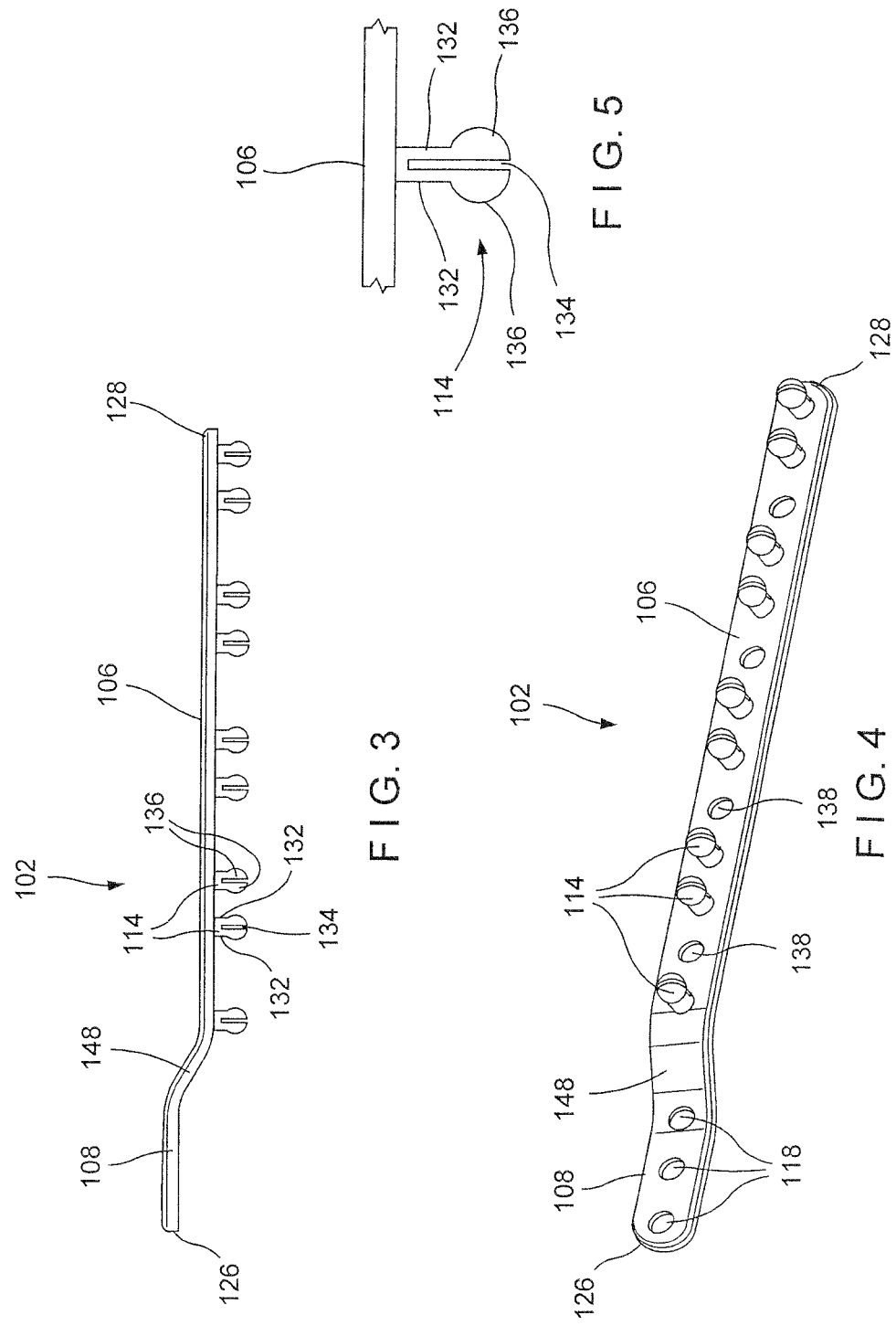

US 10,932,912 B2

PLUG IN STRUTS FOR GRAFT CAGE

PRIORITY CLAIM

The present application claims priority to U.S. Provisional Patent Application Ser. No. 62/556,786 filed on Sep. 11, 2017; the entire disclosure is expressly incorporated herein by reference.

BACKGROUND

Defects of the mandible and other bones are often treated with bone grafts and/or implants such as, bone plates, to assist with healing. Such a bone graft may, for example, be placed in a target area using any of a variety of methods. However, without a container for the bone graft, the graft material may fall away from a target site before it has been incorporated by the body into the healing bone.

SUMMARY

The present invention relates to a system for treating a bone, comprising a graft containment device extending longitudinally from a first end to a second end and including a channel extending therethrough for receiving a graft material therein, the graft containment device including a plurality of fixation openings extending therethrough, and a strut extending longitudinally from a first end to a second end and including an attaching portion configured to be attached to the graft containment device and an overhang portion configured to extend beyond one of the first and second ends, when the attaching portion is attached to the graft containment device, the attaching portion including a plurality of coupling elements for engaging the fixation openings of the graft containment device, the overhang portion including an overhang opening configured to receive a bone fixation element for fixing the strut to a bone.

The present invention also relates to a device for fixing a graft container to a bone, comprising a longitudinally extending attaching portion configured to be attached to the graft container along a length thereof, the attaching portion including a plurality of coupling elements extending therefrom along the attaching portion, each of the coupling elements configured to engage a corresponding fixation opening of the graft container and an overhang portion extending longitudinally from the attaching and configured to extend beyond one of a first end and a second end of the graft container when the attaching portion is attached to the graft container, the overhang portion including an overhang opening extending therethrough, the overhang opening configured to receive a bone fixation element therein.

The present invention also relates to a method for treating a bone, comprising packing a channel of the graft containment device with a graft material, attaching an attaching portion of a strut to a graft containment device so that an overhang portion extends beyond one of a first end and a second end of the graft containment device, coupling elements extending along the attaching portion engaging fixation openings of the graft containment device, positioning the graft containment device within a target space of a bone so that the overhang portion extends over a portion of bone to which the graft containment device is to be fixed, and inserting a bone fixation element through an overhang opening extending through the overhang portion to fix the strut and the attached graft containment device to the bone.

BRIEF DESCRIPTION

FIG. 1 shows a longitudinal side view of a system according to an exemplary embodiment of the present invention;

FIG. 2 shows another side view of the system of FIG. 1;

FIG. 3 shows a longitudinal side view of a strut of the system of FIG. 1;

FIG. 4 shows a perspective view of the strut of the system of FIG. 1; and

FIG. 5 shows an enlarged longitudinal side view of a coupling element of the strut of the system of FIG. 1.

DETAILED DESCRIPTION

The present invention may be understood with reference to the following description and the appended drawings, wherein like elements are referred to with the same reference numerals. The present invention relates to the treatment of bone and, in particular, relates to treatments using bone grafts and bone graft substitutes. Exemplary embodiments of the present invention describe a strut attachable to a graft containment cage packed with graft material and positioned at a site within which it is desired to encourage and guide the growth of new bone. The strut fixes the graft containment cage at a desired position within the target site (e.g., a gap or space in a target bone such as the mandible). The strut includes an attachable portion configured to be attached along a portion of the length of the graft cage and an overhang portion which extends beyond one of a first and second end of the graft cage to extend over a portion of bone to which the graft containment device is to be fixed. The attachable portion includes fasteners configured to be plugged-in or otherwise engaged with pores or other openings of the graft containment device. The overhang portion includes one or more openings sized and shaped to receive bone fixation elements for fixing the strut, and thereby the attached graft containment device, to the bone. Although the exemplary embodiment is shown and described in regard to the treatment of a mandible, it will be understood by those of skill in the art that the graft containment device of the present invention may also be formed in different shapes and sized to permit use in treating other types of bone which would benefit from the use of a graft containment device.

As shown in FIGS. 1-5, a system 100 for treating a bone includes a strut 102 for fixing a graft containment device 104 within a target gap or space of a bone (e.g., mandible). The strut 102 of this embodiment includes an attaching portion 106 configured to extend over a portion of the length of the graft containment device 104 in an operative position and an overhang portion 108 configured to extend beyond one of the first and second ends 110, 112, respectively, of the graft containment device 104. As would be understood by those skilled in the art, the strut 102 may be particularly useful for fixing off-the-shelf graft containment devices which may need to be cut or trimmed to fit within a target space. For example, when an off the shelf graft containment device must be cut or trimmed to fit a target space, shortening the device may entail the removal of a fixation tab for fixing the device to bone formed at an end of the graft containment device. A strut 102 may be attached to such a graft containment device to provide a mechanism for fixing the graft containment device to bone. The attaching portion 106 of the strut 102 includes a plurality of coupling elements 114 configured to engage fixation openings 144 of the graft containment device 104. The overhang portion 108 includes one or more openings 118 configured to receive bone fixation elements for fixing the strut 102, and thereby the attached graft containment device 104, to the bone.

As shown in FIGS. 1-2, the graft containment device 104 extends along a longitudinal axis from the first end 110 to the second end 112 and includes a channel 120 extending therethrough. The channel 120 may be packed with a graft material to encourage bone growth within the target space of the bone in which the graft containment device 104 is to be placed. The graft containment device 104 includes pores 116 extending laterally therethrough. The pores 116 are sized to promote vascularization while preventing graft material from falling out of the channel 120. At least some of the pores 116 may also be sized to receive a bone fixation element therethrough. In one embodiment, the graft containment device 104 may be formed of a mesh defined via, for example, a lattice of circumferential and longitudinal members 122, 124, respectively. The intersecting circumferential and longitudinal members 122, 124 may define the pores 116. A spacing between adjacent circumferential members 122 and adjacent longitudinal members 124 may be varied to vary a size of the pores 116 so that different portions of the graft containment device 104 may have different sized pores 116, as desired. A cross-sectional area of the graft containment device 104 may be shaped to substantially correspond to a portion of the bone to be replaced by the graft containment device 104. In one exemplary embodiment, the graft containment device 104 is sized and shaped to be positioned between two separated portions of a target bone. A lateral cross-section of the graft containment device 104 may substantially match an outer profile of a target portion of bone which formerly occupied the space. Where the target bone is the mandible, the cross-section of the graft containment device 104 substantially corresponds to a cross-section of a portion of the mandible to be replaced. A length of the graft containment device 104 may be trimmed to fit within the target space of the bone.

The graft containment device 104 includes a fixation portion 142 extending along a length of a surface 146 of the graft containment device 104 which, when the graft containment device 104 is positioned within the target space of, for example, a mandible, faces toward a buccal direction. The fixation portion 142 may extend substantially parallel to a longitudinal axis of the graft containment device 104 from the first end 110 to the second end 112 of the graft containment device 104. In one embodiment, ends of the of fixation portion 142 are aligned with the first and second ends 110, 112 of the graft containment device 104. In another embodiment, at least one end of the fixation portion 142 may extend beyond one of the first and second end 110, 112 of the graft containment device 104. The fixation portion 142 includes a plurality of fixation openings 144 extending therethrough, along a length thereof. As will be described in greater detail below, the fixation openings 144 are sized and shaped to receive and/or otherwise engage coupling elements 114 of the strut 102. The fixation openings 144 may also be sized and shaped to receive bone fixation elements for additional fixation of the strut 102 to the graft containment device 104 and/or for fixing the graft containment device 104 to bone. For example, where the graft containment device 104 requires a length thereof to be trimmed to fit the graft containment device 104 to the target space of the bone, one of the first and second ends 110, 112 may be trimmed so that a portion of the fixation portion 142 including a fixation opening 144 remains extending beyond the trimmed end. Thus, when the graft containment device 104 is positioned within the target space, the one of the first and second ends 110, 112 that has been trimmed may be fixed to the bone via the remaining fixation opening 144. In another embodiment, rather than fixing one end of the graft containment device 104 via a portion of the fixation portion 142 extending beyond one of the ends 110, 112 of the graft containment device 104, as described above, a second strut 102 may be attached to the fixation portion 142 so that both the first and second ends 110, 112 may be fixed to bone via struts 102.

Although the exemplary embodiment shows and describes the strut 102 as being coupled to the fixation portion 142, in another embodiment, the pores 116 may be sized and shaped to engage the coupling elements 114 so that the strut 102 may be coupled to another portion of the graft containment device 104 via the pores 116. Alternatively, a first strut 102 may be coupled to the graft containment device 104 via the fixation portion 142 while a second strut 102 is coupled to another portion of the graft containment device 104 via the pores 116. In yet another embodiment, both first and second struts 102 may be coupled to the graft containment device 104 via the pores 116. It will be understood by those of skill in the art that any number of struts 102 may be coupled to the graft containment device 104 to achieve a desired fixation of the graft containment device 104 to the bone.

In one embodiment, the graft containment device 104 further includes a plurality of laterally extending slots 130 extending thereinto, in communication with the channel 120, to define cage segments 140 separated from one another by the slots 130. For example, the slots 130 may be formed as areas in which adjacent ones of the circumferential members 122 are not coupled to one another by longitudinal members 124 about a portion of a perimeter of the graft containment device 104. The slots 130 are free of longitudinal members 124 so that the longitudinal members 124 extend only along the buccal surface 146 the graft containment device 104 in these areas. The slots 130 facilitate lateral (relative to the longitudinal axis) bending of the graft containment device 104. In particular, adjacent cage segments 140 may be moved toward one another, decreasing a size of the slot 130 extending therebetween, so that a curved path of the graft containment device 104 substantially corresponds to a curve of a portion of the mandible to be replaced.

It will be understood by those of skill in the art, however, that the graft containment device 104 is not required to include slots 130 and may include other features facilitating such bending, increasing flexibility, facilitating fixation, etc. The graft containment device 104 may have any of a variety of configurations so long as the graft containment device 104 includes openings/pores configured to receive coupling elements 114 of the strut 102.

As shown in FIGS. 3-4, the strut 102 extends longitudinally from a first end 126 to a second end 128 and includes the attaching portion 106 and the overhang portion 108. The attaching portion 106 includes coupling elements 114 and is configured to be attached to a surface of the graft containment device 104 so that the overhang portion 108 extends beyond one of the first and second ends 110, 112 of the graft containment device 104. The strut 102 may, for example, be attached to the buccal surface 146 of the graft containment device 104. A length of the attaching portion 106 may vary to extend along a desired portion of a length of the graft containment device 104. The strut 102 may also be attached to other surfaces of the graft containment device 104 such as, for example, surfaces of the graft containment device 104 corresponding to an alveolar ridge and/or a sub-mandibular region of the mandible.

The coupling elements 114 are positioned along a length of the attaching portion 106, each of the coupling elements 114 being spaced relative to one another to correspond to positions of the fixation openings 144 and/or the pores 116 along the graft containment device 104. The coupling elements 114 of this embodiment include fasteners sized and shaped to be plugged-in to correspondingly sized fixation openings 144. For example, as shown in FIG. 5, each of the coupling elements 114 may include a pair of clip arms 132 separated from one another via a slot 134 extending along a length of the clip arms 132. The clip arms 132 are biased toward a separated configuration and include enlarged ends 136. When the enlarged ends 136 are pressed against a corresponding one of the fixation openings 144, an edge of the fixation opening 144 forces the enlarged ends 136, and thereby the clip arms 132, toward one another, permitting the enlarged ends 136 to be moved through the fixation opening 144. Once the enlarged ends 136 have moved into the fixation opening 144, the clip arms 132 are free to revert to the biased separated configuration so that the enlarged ends 136 are prevented from moving out of the fixation openings 144.

In one embodiment, the enlarged ends 136 of each of the clip arms 132 form together a substantially ball shape. It will be understood by those of skill in the art that the coupling elements 114 are configured to engage the fixation openings 144 when the coupling elements 114 are pressed distally (i.e., in a direction away from a surgeon or other user) against the fixation openings 144 with a force exceeding a predetermine threshold level. In the embodiment in which the enlarged ends 136 are ball-shaped, a similar force would be required disengage the coupling elements 114 from the fixation openings 144. Alternatively, the enlarged ends 136 may be shaped so that, even when a proximal force (i.e., force in a direction toward the surgeon or other user) is exerted thereon, the enlarged ends 136 are prevented from moving toward one another to release the clip arms 132 from the corresponding one of the fixation openings 144. For example, each enlarged end 136 may include a planar proximal surface perpendicular to an axis of the element 114 which, when inserted into an opening 144 engages a portion of the graft containment device 104 surrounding the opening 144 to prevent the enlarged end 136 from passing therethrough to release the coupling element 114 from the graft containment device 104.

Although the exemplary embodiment shows and describes the coupling elements 114 as including clip arms 132 with enlarged ends 136, it will be understood by those of skill in the art that the coupling elements 114 may have any of a variety of configurations so long as each of the coupling elements 114 is configured to engage a corresponding one of the fixation openings 144. The attaching portion 106 may additionally include one or more attachment openings 138, each of which is sized and shaped to receive a bone fixation element therethrough. Thus, bone fixation elements may be inserted through one or more attachment openings 138 to provide additional fixation of the strut 102 to the graft containment device 104. A position of the one or more attachment openings 138 along the graft containment device 104 may also correspond to a position of a corresponding one of the fixation openings 144 of the graft containment device 104 so that, a bone fixation element inserted through the attachment opening 138 passes through the attachment opening 138 and into the fixation opening 144.

The overhang portion 108 extends from the attaching portion 106 so that, when the attaching portion 106 is coupled to the graft containment device 104, the overhang portion 108 extends beyond one of the first and second ends 126, 128 of the graft containment device 104. Thus, when the graft containment device 104 is positioned in the target space of the bone, the overhang portion 108 extends over a portion of bone to which the graft containment device 104 is to be fixed. The overhang portion 108 includes one or more overhang openings 118 for receiving bone fixation elements therethrough to fix the overhang portion 108 to the bone. The bone fixation element receiving overhang openings 118 may be configured to receive any of a variety of bone fixation elements such as, for example, cortical screws, locking screws and/or variable angle screws.

In one embodiment, the overhang portion 108 may be offset from the attaching portion 106 and connected thereto via a connecting portion 148 so that, when the strut 102 is attached to the graft containment device 104 and the graft containment device 104 is positioned in the target space, the graft containment device 104 may be recessed with respect to a surface of the bone to, for example, reduce tissue irritation. In other words, the overhang portion 108 extends along a plane different from a plane along which the attaching portion 106 extends. In one particular embodiment, the plane along which the overhang portion 108 extends may be substantially parallel to the plane along which the attaching portion 106 extends. It will be understood by those of skill in the art, however, that this is not required and may be varied depending on a target space to be filled and a shape of the bone to which the overhang potion 108 is to be attached.

According to an exemplary method, the graft containment device 104 may be trimmed, as desired to fit the target space of the bone. In one exemplary embodiment, the graft containment device 104 may be trimmed at one of the first and second ends 110, 112 so that a length of the graft containment device 104 substantially corresponds to the target space. The one of the first and second ends 110, 112 may be trimmed so that a portion of the fixation portion 142 including at least one fixation opening 144 remains to extend beyond one of the first and second ends 110, 112. Thus, one end of the graft containment device 104 may be fixed to the bone via the fixation portion 142 while the other end of the graft containment device 104 may be fixed to the bone via the strut 102, as described below. Once the graft containment device 104 has been trimmed, as desired, the channel 120 may be packed with a graft material.

Upon packing of the graft material, the strut 102 may be attached to the graft containment device 104 by engaging the attaching portion 106 to the graft containment device 104 so that the overhang portion 108 extends beyond one of the first and second ends 110, 112. In particular, the attaching portion 106 may be pressed against the graft containment device 104 with a force exceeding a predetermined threshold value so that each of the coupling elements 114 are pressed into a corresponding one of the fixation openings 144. In particular, enlarged ends 136 may be pressed distally against the fixation openings 144 so that the clip arms 132 are moved toward one another, thereby permitting the enlarged ends 136 to be inserted through the fixation opening 144. Once the enlarged ends 136 have been moved distally past the fixation openings 144, the clip arms 132 revert to the biased, separated configuration so that enlarged ends 136 engage a distal surface of the fixation openings 144. Where the graft containment device 104 is to be inserted into a target space of a mandible, the attaching portion 106 may be attached to the surface 146 of the graft containment device 104 which, in the operative position, faces toward a buccal direction. Where additional fixation of the strut 102 to the graft containment device 104 is desired, a bone fixation element may be inserted through one or more of the attachment openings 138, into a corresponding one of the fixation openings 144.

Once the strut 102 has been attached to the graft containment device 104, the graft containment device 104 may be positioned within the target space of the bone, between two separated portions of bone. The overhang portion 108 extends over a first portion of bone and the fixation portion 142 extends over a second portion of bone. At least one bone fixation element is inserted through one of the overhang openings 118 to fix the graft containment device 104 to the first portion of bone. At least one bone fixation element is inserted through a fixation opening 144 to fix the graft containment device 104 to the second portion of bone.

Although the exemplary method describes fixation of the graft containment device 104 to the bone via both the strut 102 and the fixation portion 142, the graft containment device 102 may be similarly fixed to the bone using more than one strut 102 so that fixation via the fixation portion 142 is not required. Additionally, as noted above, the one or more struts 102 may be attached to the graft containment device 104 via the openings 144 of the fixation portion 142 and/or the pores 116.

In addition, although the exemplary embodiment describes a strut 102 attached to a graft containment device 104 via the coupling elements 114, in another embodiment, a bone fixation plate may be similarly attached to the graft containment device 104. For example, a fixation plate including a plurality of bone fixation element receiving openings may include coupling elements, similar to the coupling elements 114, along a bone-facing surface thereof so that the fixation plate may be attached to the graft containment device 104 substantially similarly to the strut 102. In another embodiment, the graft containment device 104 may include coupling elements extending therefrom so that the coupling elements may be received within openings 138 of the strut 102 and/or bone fixation element receiving openings of a bone fixation plate.

It will be understood by those of skill in the art that modifications and variations may be made in the structure and methodology of the present invention, without departing from the spirit or the scope of the invention. Thus, it is intended that the present invention cover the modifications and variations of this invention, provided that they come within the scope of the appended claims and their equivalents.

What is claimed is:

1. A system for treating a bone, comprising:
  a graft containment device extending longitudinally from a first end to a second end and including a channel extending therethrough for receiving a graft material therein, the graft containment device including a plurality of fixation openings extending therethrough; and
  a strut extending longitudinally from a first end to a second end and including an attaching portion configured to be attached to the graft containment device and an overhang portion configured to extend beyond one of the first and second ends, when the attaching portion is attached to the graft containment device, the attaching portion including a plurality of coupling elements for engaging the fixation openings of the graft containment device, the overhang portion including an overhang opening configured to receive a bone fixation element for fixing the strut to a bone.

2. The system of claim 1, wherein the coupling element each coupling element includes a pair of clip arms separated from one another via a slot extending along a length of the clip arms, the clip arms including enlarged ends and being biased toward a separated configuration.

3. The system of claim 2, wherein the clip arms are movable so that the enlarged ends are drawn toward one another.

4. The system of claim 3, wherein the clip arms are moved when a predetermined threshold level of force is exerted thereon.

5. The system of claim 3, wherein the enlarged ends of each coupling element together form a substantially ball shape.

6. The system of claim 1, wherein the attaching portion further includes an attaching opening extending therethrough, the attaching opening sized and shaped to receive a bone fixation element therethrough.

7. The system of claim 6, wherein the attachment opening is positioned along the attaching portion between two adjacent coupling elements.

8. The device of claim 7, wherein the attachment opening is positioned along the attaching portion between two adjacent coupling elements.

9. The system of claim 1, wherein the overhang portion extends along a plane offset from a plane along which the attaching portion extends.

10. The system of claim 9, wherein the plane along which the overhang portion extends is substantially parallel to the plane along which the attaching portion extends.

11. The system of claim 1, wherein the graft containment device is formed of a mesh material including a lattice of circumferential members and longitudinal members intersecting one another to define a plurality of pores.

12. The system of claim 1, wherein the graft containment device includes a fixation portion extending along a length thereof, the fixation portion including the plurality of fixation openings therealong.

13. A device for fixing a graft container to a bone, comprising:
  a longitudinally extending attaching portion configured to be attached to the graft container along a length thereof, the attaching portion including a plurality of coupling elements extending therefrom along the attaching portion, each of the coupling elements configured to engage a corresponding fixation opening of the graft container; and
  an overhang portion extending longitudinally from the attaching and configured to extend beyond one of a first end and a second end of the graft container when the attaching portion is attached to the graft container, the overhang portion including an overhang opening extending therethrough, the overhang opening configured to receive a bone fixation element therein.

14. The device of claim 13, wherein each coupling element includes a pair of clip arms separated from one another via a slot extending along a length of the clip arms, the clip arms including enlarged ends and being biased toward a separated configuration.

15. The device of claim 14, wherein the clip arms are movable so that the enlarged ends are drawn toward one another.

16. The device of claim 15, wherein the clip arms are moved when a predetermined threshold level of force is exerted thereon.

17. The device of claim 15, wherein the enlarged ends of each coupling element together form a substantially ball shape.

18. The device of claim 13, wherein the attaching portion further includes an attaching opening extending therethrough, the attaching opening sized and shaped to receive a bone fixation element therethrough.

19. The device of claim 13, wherein the overhang portion extends along a plane offset from a plane along which the attaching portion extends.

20. The device of claim 19, wherein the graft containment device includes a fixation portion extending along a length thereof, the fixation portion including the plurality of fixation openings therealong.

* * * * *